United States Patent [19]
Pitchai et al.

[11] Patent Number: 5,874,652
[45] Date of Patent: Feb. 23, 1999

[54] PROCESS FOR HYDROGENATING AQUEOUS ALDEHYDE MIXTURES

[75] Inventors: Rangasamy Pitchai; Thomas S. Zak, both of West Chester, Pa.

[73] Assignee: Arco Chemical Technology, L.P., Greenville, Del.

[21] Appl. No.: 138,780

[22] Filed: Oct. 18, 1993

[51] Int. Cl.[6] .................................................. C07C 29/38
[52] U.S. Cl. ........................ 568/862; 568/881; 549/509
[58] Field of Search .................................. 568/862, 881; 549/509

[56] References Cited

U.S. PATENT DOCUMENTS

| | | | |
|---|---|---|---|
| 3,284,517 | 11/1966 | Rylander et al. | 260/638 |
| 4,083,882 | 4/1978 | Taylor et al. | 260/635 R |
| 4,263,449 | 4/1981 | Saito et al. | 560/263 |
| 4,879,420 | 11/1989 | Ernst | 568/617 |
| 4,933,473 | 6/1990 | Ninomiya et al. | 568/862 |

FOREIGN PATENT DOCUMENTS

| | | | |
|---|---|---|---|
| 7101 | 1/1980 | European Pat. Off. | 568/862 |

OTHER PUBLICATIONS

J. Catalysis 124 (1990) (Miura et al) "The Control of Metal Precursor Mobilities as Variable in the Preparation of Supported etc.".

J.Catalysis 124 (1990) (Alerasool et al.) "Preparation and Characterization of Support Pt–Ru Bimetallic Clusters: etc.".

Langmuir 4 (1988) 1083 (Alerasool et al.) "The Role of Preparative Variables on the Surface Composition of Supported etc.".

Nouveau J. de Chemie 4 (1980) 677 (Gomez et al.) "Catalytic Properties of Platinum–Ruthenium Catalysts".

*Primary Examiner*—Rebecca Cook
*Attorney, Agent, or Firm*—Jonathan L. Schuchardt

[57] ABSTRACT

A process for hydrogenating aqueous mixtures of 4-hydroxybutanal and 3-hydroxy-2-methylpropanal is disclosed. The process uses a metallic Pt—Ru catalyst supported on γ-alumina. The process gives improved yields of 2-methyl-1,3-propanediol while minimizing the formation of unwanted by-products such as isobutyl alcohol and tetrahydrofuran.

20 Claims, No Drawings

PROCESS FOR HYDROGENATING AQUEOUS ALDEHYDE MIXTURES

FIELD OF THE INVENTION

The invention relates to processes for catalytic hydrogenation of hydroxyaldehydes. In particular, the invention is a process for hydrogenating aqueous mixtures of 4-hydroxybutanal and 3-hydroxy-2-methylpropanal with a supported bimetallic catalyst to produce 1,4-butanediol and 2-methyl-1,3-propanediol.

BACKGROUND OF THE INVENTION

One commercial process for manufacturing 1,4-butanediol involves isomerization of propylene oxide to allyl alcohol, rhodium-catalyzed hydroformylation of allyl alcohol to 4-hydroxybutanal, and catalytic hydrogenation of 4-hydroxybutanal to give 1,4-butanediol. Hydroformylation of allyl alcohol gives, in addition to 4-hydroxybutanal, a substantial proportion of 3-hydroxy-2-methylpropanal. The aldehyde products are extracted into water, and are hydrogenated in aqueous media using a Raney nickel catalyst to give 1,4-butanediol and 2-methyl-1,3-propanediol.

Raney nickel, a powdered catalyst, is useful for a slurry-type hydrogenation process, but not for a fixed-bed process. A goal in the field is to develop aqueous hydrogenation catalysts that are useful for a fixed-bed process. A large capital savings is potentially available in switching from a conventional slurry process to a fixed-bed process, and this potential savings provides a substantial incentive to develop viable catalyst systems useful for a fixed-bed process. Unfortunately, most fixed-bed supports are acidic, and tend to promote undesirable dehydration of 3-hydroxy-2-methylpropanal. Fixed-bed catalyst systems that give high selectivity to 2-methyl-1,3-propanediol are needed.

U.S. Pat. Nos. 4,083,882 (Taylor et al.) and 4,263,449 (Saito et al.) teach hydrogenation of aqueous 4-hydroxybutanal/3-hydroxy-2-methylpropanal mixtures using slurry-phase Raney nickel catalysts, but do not teach to use aqueous hydrogenation catalysts useful for a fixed-bed process.

Relatively acidic aqueous hydrogenation catalysts tend to catalyze unwanted cyclodehydration reactions. For example, when 4-hydroxybutanal is hydrogenated to give 1,4-butanediol, some of the 1,4-butanediol can cyclodehydrate to give tetrahydrofuran. Tetrahydrofuran may, in fact, be the desired end product; however, the manufacturer would like to be able to control the process to produce exclusively either 1,4-butanediol or tetrahydrofuran. Thus, hydrogenation catalyst systems that can minimize the amount of tetrahydrofuran produced in a 1,4-butanediol process are desirable.

U.S. Pat. No. 4,933,473 (Nimomiya et al.) teaches a process for producing neopentyl glycol by hydrogenating hydroxypivaldehyde in aqueous media in the presence of a platinum—ruthenium—tungsten (Pt—Ru—W) catalyst system. The reference teaches that the Pt—Ru—W catalyst has a higher activity and longer service life than catalysts containing Pt and Ru, either singly or in combination (column 2, lines 64–68). The reference does not address the problem of dehydration of 3-hydroxy-2-methylpropanal during hydrogenation of 4-hydroxybutanal/3-hydroxy-2-methylpropanal mixtures. In fact, because hydroxypivaldehyde lacks a hydrogen β- to the hydroxyl group, dehydration cannot occur with hydroxypivaldehyde.

An improved process for hydrogenation of aqueous hydroxyaldehydes is needed. Preferably, the catalyst used in the process would have good activity and little tendency to promote dehydration of 3-hydroxy-2-methylpropanal or cyclodehydration of 1,4-butanediol so that yields of 2-methyl-1,3-propanediol would be high, and formation of isobutyl alcohol and tetrahydrofuran would be minimized. A process that could use a fixed-bed catalyst would save capital expenses and simplify product separation.

SUMMARY OF THE INVENTION

The invention is a process for hydrogenating an aqueous mixture of 4-hydroxybutanal and 3-hydroxy-2-methylpropanal. The process comprises hydrogenating the aqueous aldehyde mixture in the presence of a catalyst system that consists essentially of platinum and ruthenium supported on γ-alumina. The product mixture contains 1,4-butanediol, 2-methyl-1,3-propanediol, and less than about 0.1 moles of isobutyl alcohol per mole of 2-methyl-1,3-propanediol.

We have found that the γ-alumina-supported Pt—Ru catalysts are more active than either Pt or Ru catalysts alone. In addition, the use of γ-alumina as a support results in good catalyst activity and high selectivity to the desired products, particularly 2-methyl-1,3-propanediol. Formation of unwanted by-products such as isobutyl alcohol and tetrahydrofuran is minimized. Unlike powdered Raney nickel catalysts, the γ-alumina-supported Pt—Ru catalysts of the invention can be used in a fixed-bed process.

DETAILED DESCRIPTION OF THE INVENTION

An aqueous mixture of 4-hydroxybutanal and 3-hydroxy-2-methylpropanal is hydrogenated in the process of the invention. The aldehydes can be present in any desired proportion. A preferred aqueous aldehyde mixture for use in the process of the invention is the aqueous aldehyde mixture obtained in the commercial process for hydroformylation of allyl alcohol. This mixture typically contains mostly 4-hydroxybutanal with a smaller proportion of 3-hydroxy-2-methylpropanal. The aldehydes are commonly separated from the rhodium catalyst used in their manufacture by extraction of the organic reaction mixture with water.

The skilled person can adjust the concentration of aldehydes in the aqueous mixture to suit his needs; however, preferred aqueous 4-hydroxybutanal/3-hydroxy-2-methylpropanal mixtures will have from about 1 to about 20 wt. % aldehydes. More preferred aqueous mixtures will contain from about 5 to about 15 wt. % aldehydes.

The catalyst system used in the process of the invention consists essentially of platinum and ruthenium supported on γ-alumina. When either platinum or ruthenium is used alone, lower aldehyde conversions or poorer diol selectivities result. Including a third metal such as tungsten (see U.S. Pat. No. 4,933,473) provides no additional improvement in diol selectivity, and actually gives more isobutyl alcohol compared with the Pt—Ru catalyst.

Although the platinum and ruthenium can be present in the catalyst system in any desired ratio, it is preferred that the weight ratio of ruthenium to platinum be within the range of about 0.1:1 to about 10:1. A more preferred range is from about 0.4:1 to about 1:1.

The platinum—ruthenium catalysts can be prepared from any suitable source of the metals, including, for example, halide, nitrate, sulfate, and carbonate salts, oxides, hydroxides, acid salts, and carbonyl complexes. Generally, the catalysts are prepared by combining aqueous solutions or suspensions of the metal compounds with γ-alumina, and driving off the water to obtain a supported catalyst system. Any other suitable method for supporting transition metals on solid supports can be used. Suitable methods of catalyst preparation are described, for example, in Miura et al., *J. Catalysis* 124 (1990) 194; Alerasool et al., *J. Catalysis* 124 (1990) 204; Alerasool et al., *Langmuir* 4 (1988) 1083; and Gomez et al., *Nouveaux J. de Chimie* 4 (1980) 677. Following evaporation of water from the supported catalyst system, the supported catalyst is usually dried at a temperature within the range of about 80° C. to about 200° C., preferably from about 80° C. to about 120° C. If desired, the dried catalyst can be calcined at a temperature within the range of about 200° C. to about 500° C., preferably from about 250° C. to about 400° C. prior to use.

The support used for the catalyst system is γ-alumina. We have found that γ-alumina gives better activity and diol selectivity than other common supports such as α-alumina, silica, carbon, calcium silicate, and mixtures of these. When supports other than γ-alumina are used, selectivity to isobutyl alcohol exceeds about 0.1 moles per mole of 2-methyl-1,3-propanediol used. In addition, aldehyde conversion decreases when other supports are used. Aldehyde conversions in excess of 90% are common with γ-alumina, but are not ordinarily achievable with other common catalyst supports. See Examples 4 and C7–C10 below, which demonstrate the importance of using γ-alumina as a support for both aldehyde conversion and isobutyl alcohol selectivity.

The supported catalyst system preferably contains from about 0.1 to about 5 wt. % of ruthenium and platinum metals based on the total amount of supported catalyst system. A more preferred range is from about 0.1 to about 1.5 wt. % metals. Amounts of ruthenium and platinum in excess of 5 wt. % provide no additional benefit, while amounts less than about 0.1 wt. % are generally insufficient to give satisfactory reaction rates.

The process of the invention can be performed batchwise, semi-batchwise, or continuously as desired. Optimum aldehyde conversions and 2-methyl-1,3-propanediol yields are obtained when a stirred-tank reactor system is used. The catalyst system can also be used for a fixed-bed process or trickle-bed process, however, and these processes are preferred for commercial use because of the large potential capital savings available from using them.

The hydrogenation process of the invention can be performed over a broad range of temperatures. Preferably, the process is performed at a temperature within the range of about 60° C. to about 150° C. A more preferred range is from about 80° C. to about 120° C.

The hydrogen pressure can be adjusted to suit the needs of the manufacturer. Preferably, a relatively high hydrogen pressure is used. A preferred range is from about 500 to about 2000 psi. Lower pressures are generally less preferred because substantial catalyst poisoning can occur when pressures less than about 500 psi are used. If desired, hydrogen can be continuously sparged through the reactor while maintaining a relatively high hydrogen pressure, as in the semi-batch process illustrated below (see Examples 1–3).

The process of the invention makes it possible to hydrogenate aqueous mixtures of 4-hydroxybutanal and 3-hydroxy-2-methylpropanal and obtain relatively high yields of 2-methyl-1,3-propanediol. More than 90% of the 3-hydroxy-2-methylpropanal is typically converted to 2-methyl-1,3-propanediol, while aldehyde conversions are maintained at greater than about 90%.

The process of the invention also gives relatively high selectivity to 1,4-butanediol. Cyclodehydration of 1,4-butanediol is minimized, and tetrahydrofuran selectivities of less than about 0.01 moles per mole of 1,4-butanediol produced are typical.

The following examples merely illustrate the invention. Those skilled in the art will recognize many variations that are within the spirit of the invention and scope of the claims.

EXAMPLE A

Preparation of γ-Alumina-supported Platinum-Ruthenium Catalyst

Hydrogen hexachloroplatinate(IV) (0.424 g) is dissolved in 50% hydrochloric acid (200 mL) in a round-bottom flask. Ruthenium trichloride hydrate (0.331 g) is added, and the mixture is heated and stirred until the salts dissolve completely. Norton SA-6173 γ-alumina (40 g) is added to the flask, and the mixture is evaporated to dryness using a rotary evaporator. The supported Pt—Ru catalyst residue is dried in an oven at 100° C. for 9 h, then calcined at 300° C. for 5 h, cooled to room temperature, and stored.

The catalyst is placed in a reduction tube, and the tube is placed in a reduction oven. The oven is purged with nitrogen (100 mL/min) for 30 min. at room temperature. The nitrogen flow is stopped, and hydrogen flow (50 mL/min) is started. The oven temperature is slowly increased to 300° C., and is kept at 300° C. for 5 h. The catalyst is cooled under a stream of nitrogen to room temperature. A syringe is used to inject small pulses of air into the nitrogen flow. The injection is repeated about 10 times. The nitrogen flow is then discontinued, and the catalyst is stored.

EXAMPLES 1–3

Hydrogenation of 4-Hydroxybutanal/3-Hydroxy-2-Methylpropanal Semi-Batch Process

γ-Alumina-supported Pt, Ru, or Pt—Ru Catalyst

A 300-mL stirred autoclave reactor is charged with aqueous 4-hydroxybutanal/3-hydroxy-2-methylpropanal mixture (15 wt. % aldehydes in water, 7:1 ratio of aldehydes, 150 mL). A γ-alumina-supported Pt, Ru, or Pt—Ru catalyst that contains 0.9 wt. % total metals (1.0 g), prepared by the method of Example A, is added to the reactor. Hydrogen flow through the reactor is adjusted to 300 mL/min, and the hydrogen pressure is maintained at 750 psig. The mixture is heated at 100° C. for 3 h. The mixture is cooled to room temperature, and is analyzed by gas chromatography (GC) to determine the extent of aldehyde conversion and the product composition. The results of the GC analysis appear in Table 1. The results from this semi-batch experiment demonstrate that a combined platinum—ruthenium catalyst is more active for hydrogenating aqueous aldehyde mixtures than an equivalent amount of either a ruthenium or platinum catalyst alone.

EXAMPLES 4–6

Hydrogenation of 4-Hydroxybutanal/3-Hydroxy-2-Methylpropanal Continuous Stirred-Tank Reaction Process

EXAMPLES 4

γ-Alumina-supported Pt—Ru Catalyst

A 500-mL continuous stirred-tank reactor is used for hydrogenation. The γ-alumina-supported Pt—Ru catalyst prepared in Example A (17.9 g) is loaded into a basket that is attached to the stirrer shaft. The reactor is initially filled with water, and the catalyst is reduced with hydrogen gas at 100° C. and 750 psig for 8 h. An aqueous mixture of 4-hydroxybutanal and 3-hydroxy-2-methylpropanal (15 wt. % aldehydes, 7:1 ratio of 4-hydroxybutanal to 3-hydroxy-2-methylpropanal) is then fed to the reactor at a rate of 2.5 LHSV while maintaining a 2:1 $H_2$ to total aldehydes ratio. After 8 h on stream, samples are periodically removed from the reactor and are analyzed by gas chromatography to determine aldehyde conversion and selectivity to diols and other products. Hydrogenation results appear in Table 2.

COMPARATIVE EXAMPLE 5

γ-Alumina-supported Pt Catalyst

The procedure of Example 4 is followed except that the supported catalyst contains 0.9 wt. % of platinum and no ruthenium. The catalyst is prepared as in Example A, but without the ruthenium compound. Hydrogenation results appear in Table 2. The results show the favorable impact on aldehyde conversion and by-product selectivity of using the bimetallic Pt—Ru catalyst system compared with platinum alone in a stirred-tank process.

COMPARATIVE EXAMPLE 6

γ-Alumina-supported Pt—Ru—W Catalyst

The procedure of Example 4 is followed except that the supported catalyst contains 0.5 wt. % platinum, 0.4 wt. % ruthenium, and 0.02 wt. % of tungsten. This catalyst is prepared by including ammonium metatungstate (0.011 g) in the catalyst preparation method of Example A. Hydrogenation results appear in Table 2. The results suggest that there is nothing to be gained by including tungsten in the supported catalyst system, since aldehyde conversion and product selectivity are poorer in this example than in Example 4, in which tungsten is not included.

COMPARATIVE EXAMPLES 7–10

Pt—Ru Catalyst: Effect of Support Type

The procedure of Example 4 is followed except that the platinum—ruthenium catalyst is supported on a variety of supports other than γ-alumina. The supports used and the results of the hydrogenations are listed in Table 3. The results show that γ-alumina is the best support for giving both high aldehyde conversions (>90%) and good yields of 1,4-butanediol and 2-methyl-1,3-propanediol, as is evidenced by low selectivities to the isobutyl alcohol and tetrahydrofuran by-products.

TABLE 1

Hydrogenation Results: Semi-Batch Results
γ-Alumina-Supported Catalysts

| Ex # | Catalyst (wt. % Metals) | React. time (h) | HBA % Conversion | HMPA % Conversion | IBA % Selectivity | X-13 % Selectivity |
|---|---|---|---|---|---|---|
| C1 | Pt (0.9) | 3 | 21 | 79 | 7.5 | 27 |
| C2 | Ru (0.9) | 3 | 38 | 84 | 16 | 25 |

TABLE 1-continued

Hydrogenation Results: Semi-Batch Results
γ-Alumina-Supported Catalysts

| Ex # | Catalyst (wt. % Metals) | React. time (h) | HBA % Conversion | HMPA % Conversion | IBA % Selectivity | X-13 % Selectivity |
|---|---|---|---|---|---|---|
| 3 | Pt—Ru (0.5/0.4) | 3 | 65 | 93 | 15 | 17 |

HBA = 4-hydroxybutanal;
HMPA = 3-hydroxy-2-methylpropanal;
IBA = isobutyl alcohol;
X-13 = 2-(4-hydroxybutoxy)tetrahydrofuran

TABLE 2

Hydrogenation Results: Stirred-Tank Reactor
γ-Alumina-Supported Catalysts

| Ex # | Catalyst (wt. % Metals) | Time (h) on stream | HBA % Conversion | HMPA % Conversion | IBA % Selectivity | THF % Selectivity |
|---|---|---|---|---|---|---|
| 4 | Pt—Ru (0.5/0.4) | 11 | 94 | 100 | 4.3 | 0.5 |
|   |   | 28 | 91 | 96 | 8.7 | 0.9 |
| C5 | Pt (0.9) | 11 | 63 | 79 | 24 | 6.4 |
|   |   | 30 | 55 | 77 | 33 | 10 |
| C6 | Pt—Ru—W (0.5/0.4/0.02) | 10 | 89 | 95 | 9.6 | 0 |
|   |   | 28 | 84 | 92 | 14 | 0 |

HBA = 4-hydroxybutanal;
HMPA = 3-hydroxy-2-methylpropanal;
IBA = isobutyl alcohol;
THF = tetrahydrofuran

TABLE 3

Hydrogenation Results: Stirred-Tank Reactor
Platinum-Ruthenium Catalyst
Effect of Catalyst Support

| Ex # | Catalyst Support | Time (h) on stream | HBA % Conversion | HMPA % Conversion | IBA % Selectivity | THF % Selectivity |
|---|---|---|---|---|---|---|
| 4 | γ-Alumina | 11 | 94 | 100 | 4.3 | 0.5 |
|   |   | 28 | 91 | 96 | 8.7 | 0.9 |
| C7 | α-Alumina/silica | 10 | 72 | 83 | 5.2 | 1.2 |
| C8 | Silica (No HCl) | 10 | 60 | 76 | 11 | 4.0 |
| C9 | Silica (HCl) | 11 | 63 | 65 | 23 | 5.0 |
| C10 | Calcium silicate/silica | 11 | 59 | 81 | 42 | 2.4 |

HBA = 4-hydroxybutanal;
HMPA = 3-hydroxy-2-methylpropanal;
IBA = isobutyl alcohol;
THF = tetrahydrofuran The preceding examples are meant as illustrations. The invention is defined by the following claims.

We claim:

1. A process which comprises hydrogenating an aqueous mixture of 4-hydroxybutanal and 3-hydroxy-2-methylpropanal in the presence of a catalyst system that consists essentially of platinum and ruthenium supported on γ-alumina to produce 1,4-butanediol, 2-methyl-1,3-propanediol, less than about 0.01 moles of tetrahydrofuran per mole of 1,4-butanediol, and less than about 0.1 moles of isobutyl alcohol per mole of 2-methyl-1,3-propanediol.

2. The process of claim 1 wherein the aqueous mixture contains from about 1 to about 20 wt. % aldehydes.

3. The process of claim 1 wherein the weight ratio of ruthenium to platinum in the catalyst system is within the range of about 0.1:1 to about 10:1.

4. The process of claim 1 wherein the total amount of ruthenium and platinum used in the supported catalyst system is within the range of about 0.1 to about 5 wt. % based on the amount of supported catalyst system.

5. The process of claim 1 wherein the process is performed in a stirred-tank reactor.

6. The process of claim 1 wherein the process is performed in a fixed-bed reactor.

7. The process of claim 1 wherein the hydrogenation is performed at a temperature within the range of about 60° C. to about 150° C.

8. The process of claim 1 wherein the hydrogenation is performed at a pressure within the range of about 500 to about 2000 psi.

9. The process of claim 1 wherein conversion of both aldehydes exceeds about 90 percent.

10. A process which comprises hydrogenating an aqueous mixture of 4-hydroxybutanal and 3-hydroxy-2-methylpropanal in a stirred-tank reactor in the presence of a catalyst system that consists essentially of platinum and ruthenium supported on γ-alumina to produce 1,4-butanediol, 2-methyl-1,3-propanediol, less than about 0.01 moles of tetrahydrofuran per mole of 1,4-butanediol and less than about 0.1 moles of isobutyl alcohol per mole of 2-methyl-1,3-propanediol; wherein the weight ratio of ruthenium to platinum in the catalyst system is within the range of about 0.1:1 to about 10:1.

11. The process of claim 10 wherein the aqueous mixture contains from about 1 to about 20 wt. % aldehydes.

12. The process of claim 10 wherein the weight ratio of ruthenium to platinum in the catalyst system is within the range of about 0.4:1 to about 1:1.

13. The process of claim 10 wherein the total amount of ruthenium and platinum used in the supported catalyst system is within the range of about 0.1 to about 5 wt. % based on the amount of supported catalyst system.

14. The process of claim 10 wherein conversion of both aldehydes exceeds about 90 percent.

15. A process which comprises hydrogenating an aqueous mixture of 4-hydroxybutanal and 3-hydroxy-2-methylpropanal in a stirred-tank reactor in the presence of a catalyst system that consists essentially of platinum and ruthenium supported on γ-alumina to produce 1,4-butanediol, 2-methyl-1,3-propanediol, less than about 0.01 moles of tetrahydrofuran per mole of 1,4-butanediol, and less than about 0.1 moles of isobutyl alcohol per mole of 2-methyl-1,3-propanediol; wherein the weight ratio of ruthenium to platinum in the catalyst system is within the range of about 0.1:1 to about 10:1; and wherein the total amount of ruthenium and platinum used in the supported catalyst system is within the range of about 0.1 to about 5 wt. % based on the amount of supported catalyst system.

16. The process of claim 15 wherein the aqueous mixture contains from about 5 to about 15 wt. % aldehydes.

17. The process of claim 15 wherein the weight ratio of ruthenium to platinum in the catalyst system is within the range of about 0.4:1 to about 1:1.

18. The process of claim 15 wherein the total amount of ruthenium and platinum used in the supported catalyst system is within the range of about 0.1 to about 1.5 wt. % based on the amount of supported catalyst system.

19. The process of claim 15 wherein the hydrogenation is performed at a temperature within the range of about 80° C. to about 120° C.

20. The process of claim 15 wherein conversion of both aldehydes exceeds about 90 percent.

* * * * *